(12) United States Patent
Emery et al.

(10) Patent No.: US 6,331,417 B1
(45) Date of Patent: Dec. 18, 2001

(54) DETECTION AND QUANTIFICATION OF HUMAN HERPES VIRUS 7 BY ENZYMIC AMPLIFICATION

(75) Inventors: Vincent C Emery; Paul Griffiths, both of London (GB)

(73) Assignee: Royal Free Hospital School of Medicine, London (GB)

(*) Notice: Subject to any disclaimer, the term of this patent is extended or adjusted under 35 U.S.C. 154(b) by 0 days.

(21) Appl. No.: 08/981,653

(22) PCT Filed: Jul. 12, 1996

(86) PCT No.: PCT/GB96/01660

§ 371 Date: Jan. 8, 1998

§ 102(e) Date: Jan. 8, 1998

(87) PCT Pub. No.: WO97/03345

PCT Pub. Date: Jan. 30, 1997

(30) Foreign Application Priority Data

Jul. 13, 1995 (GB) .................................................. 9514325

(51) Int. Cl.[7] .............................. C12P 19/34; C12Q 1/68; C07H 21/04
(52) U.S. Cl. ......................... 435/91.32; 435/91.3; 435/6; 536/23.1; 536/23.72; 536/24.3; 536/24.33
(58) Field of Search ................................ 536/23.1, 23.72, 536/24.3, 24.33; 435/91.2, 91.32

(56) References Cited

FOREIGN PATENT DOCUMENTS

| | | |
|---|---|---|
| WO-A-9201816 | 2/1992 | (WO) . |
| WO-A-9400140 | 1/1994 | (WO) . |
| WO-A-9410344 | 5/1994 | (WO) . |

OTHER PUBLICATIONS

Journal Of Medical Virology, vol. 45, Mar. 1995, pp. 282–283, Portolani M. et al: "Isolation of human Herpesvirus 7 from an infant with Febrile Syndrome".

Archives Of Virology, vol. 136, 1994, pp. 183–190, Yalcin S. et al: "Human herpesvirus 6 and human herpesvirus 7 infections in renal transplant recipients and healthy adults in Turkey".

Pediatrics, vol. 95, No. 2, Feb. 1995, pp. 187–190, Asano Y. et al: "Clinical features and viral excretion in an infant with primary human herpesvirus 7 infection".

Hepatology, vol. 19, No. 5, May 1994, pp. 871–875, Naito M. et al: "Serum hepatitus c virus RNA quantity and histological features of hepatitis c virus carriers with persistently normal ALT levels".

Genetic Analysis Techniques And Applications, vol. 11, No. 1, 1994, pp. 1–6, Clementi M. et al: "Competitive polymerase chain reaction and analysis of viral activity at the molecular level".

Medical Sciences, vol. 89, Nov. 1992, pp. 10552–10556, Proc. Natl. Acad. Sci. USA, Berneman Z. et al: "Human herpesvirus 7 is an T–lymphtropic virus and is related to, but significantly different from, human herpesvirus 6 and human cytomegalovirus".

Medical Sciences, vol. 87, Jan. 1990, pp. 748–752, Proc. Natl. Acad. Sci. USA, Frenkel N. et al: "Isolation of a new herpesvirus from human $DC4^+T$ cells".

Journal Of Virology, Nov. 1991, pp. 6260–6265, Wyatt L. et al: "Human Herpesvirus 7: Antigenic Properties and Prevalence in Children and Adults".

*Primary Examiner*—David Guzo
*Assistant Examiner*—Gerald G. Leffers, Jr.
(74) *Attorney, Agent, or Firm*—Nixon & Vanderhye P.C.

(57) ABSTRACT

The present invention relates to an isolated nucleic acid molecule comprising: (i) a primer protion consisting of a contiguous sequence of from 10 to 50 nucleotides capable of hybridizing to (a) the target nucleic acid molecule represented by SEQ ID NO:1, or (b) to the complementary stand thereof; and optional (ii) a further portion comprising from 1 to 25 nucleotides joined to and immediately 5' to the 5' end of the primer portion.

27 Claims, 6 Drawing Sheets

DETECTION AND QUANTIFICATION OF HUMAN HERPES VIRUS 7 BY ENZYMIC AMPLIFICATION

This invention was made with US government support under grant number A133389-02 ("significance of HHV6–7 for immunocompromised patients") awarded by the National Institutes of Health, Bethesda, Md. 20892, USA. The US Government has certain rights in the invention.

This invention relates to a method for detecting and quantifying the presence of human herpesvirus 7 (HHV-7) in a sample, and to nucleic acid sequences useful in such a method.

HHV-7 is a member of the family Herpesviridae and is related to but genetically distinct from human herpesviruses 6A and 6B (HHV-6A and HHV-6B). HHV-7 was first isolated in 1989 and subsequently found to be present in the saliva of from 75% to over 90% of healthy adult humans (Frenkel et al (1990): PNAS 87, 748–752; Wyatt et al (1991): J. Virol. 65(11), 6250–6265).

HHV-7 has been found to cause an exanthem subitum-type illness in some children, one symptom of this illness being the development of rashes and acute febrile illness. At present, other disease symptoms attributable to HHV-7 have not been identified but, by analogy with other human herpesviruses, HHV-7 can be expected to cause disease, especially in immunocompromised hosts, such as organ transplant recipients. Therefore, it is desirable to be able to detect and quantify the presence of HHV-7 in samples of human tissue and bodily fluids. Until now, methods of detecting HHV-7 have been serological in nature, relying on the use of antibodies to HHV-7 proteins. These methods are, however, unsatisfactory. This is because they fail to quantify HHV-7, or have low specificity for HHV-7 with respect to other viruses such as HHV-6A/B.

The inventors have identified a sequence of HHV-7 DNA that is unique to this virus and not found in other related viral genomes although it codes for a protein that has some sequence homology with the product of KA3L gene of HHV6. The unique sequence is a 193 base pair fragment of HHV-7 DNA, and was identified by digestion of purified HHV-7 DNA with a restriction endonuclease, followed by cloning the restriction fragments into a plasmid vector. Using the sequence of this 193 base pair "target" fragment, it has been possible to synthesise a variety of primers that hybridise to it over part of its length. These can be used in Polymerase Chain Reaction (PCR), including nested PCR reactions, to amplify the 193 base pair fragment.

The inventors have also prepared a mutant DNA control sequence based on the 193 base pair fragment. This construct has internal substitutions that provide an additional restriction site (for the restriction endonuclease SmaI) that is absent from the target sequence. Primers suitable for construction of the mutant sequence by PCR amplification have also been synthesised.

The mutant control sequence can therefore act as a target sequence mimetic for the 193 base pair fragment in any PCR reaction performed on a sample containing the 193 base pair sequence and the control sequence. This forms the basis of a method of detecting and quantifying the presence of the 193 base pair fragment in samples, for example samples of human tissue or bodily fluids, and thus quantifying HHV-7 in these samples. A known amount of the control sequence is added to the sample; a pair of primers is also added and PCR is performed. As the target and control sequences are very similar, and preferably identical at the primer binding sites, one pair of primers allows the amplification of both the 193 base pair target sequence and the control sequence by PCR. Cleavage of the mutant sequence with the restriction endonuclease SmaI, which does not cleave the 193 base pair wild-type sequence, followed by quantification of the cleavage products then allows the amount of the target sequence present to be determined as the amount of the control sequence added is known. This, in turn, allows the presence of the HHV-7 virus in the sample be quantified as each HHV-7 genome comprises one target sequence.

As the target sequence is unique to HHV-7, this method can be used to quantify HHV-7 accurately in samples, thus potentially providing information as to the likelihood of the sample donor suffering from the symptoms caused by the virus.

Accordingly, the invention provides:

An isolated nucleic acid molecule comprising (i) a primer portion consisting of a contiguous sequence of from 10 to 50 nucleotides capable of hybridising to (a) the target nucleic acid molecule represented by SEQ ID NO:1 or (b) to the complementary stand thereof; and optionally (ii) a further portion comprising from 1 to 25 nucleotides joined to and immediately 5' to the 5' end of the primer portion;

a pair of nucleic acid molecules as defined above wherein one nucleic acid molecule has a primer region of type (a) as defined above and the other nucleic acid molecule has a primer region of type (b) as defined above; and wherein the two primers in combination are capable of amplifying the target nucleic acid molecule represented by SEQ ID NO:1 or a section thereof in a polymerase chain reaction;

a pair of nucleic acid molecules as defined above that hybridise respectively to the target nucleic acid sequence of SEQ ID NO:1 and its complementary stand in such positions that the 5' end of the each primer region hybridises at a location that is from 0 to 50 nucleotides 3' to the 5' end of the sequence of SEQ ID NO:1 or the complementary strand thereto;

A method of determining the amount of a target nucleic acid having the sequence shown in SEQ ID NO:1 in a sample which method comprises:

(i) mixing the sample with a predetermined amount of control nucleic acid;

(ii) bringing the mixture formed in (i) into contact with at least one nucleic acid primer as defined above that is capable of hybridising to the target nucleic acid and at least one primer as defined above that is capable of hybridising to the control nucleic acid;

(iii) performing a nucleic acid amplification reaction, which reaction requires the presence of the primers defined in (ii) to amplify the target nucleic acid sequence or a section thereof and the control nucleic acid or a section thereof;

(iv) determining the relative quantities of the amplified control and target nucleic acids; and (v) calculating from the determination of (iv) the amount of target nucleic acid in the sample;

An isolated nucleic acid sequence selected from the sequences shown in SEQ ID NO:1 and SEQ ID NO:2, or the complementary strands thereof; and A kit for quantification of human herpesvirus 7 (HV-7) in a sample by means of a method as defined above which kit comprises:

(i) a control nucleic acid as defined above;

(ii) one or more pairs of primers as defined above that are suitable for amplifying both the target and control nucleic acid sequences.

The target sequence that is amplified in methods of the invention is the 193 base pair sequence of SEQ ID NO:1 or a section of it, preferably the entire 193 base pair sequence or the section thereof shown in SEQ ID NO:1. Where the target sequence is a section of the sequence of SEQ ID NO:1, the section may be of any length provided that the section in question is unique to the HHV-7 genome, in the sense that it is not found in the genomes of other viruses, particularly HHV-6A and HHV6B, that infect human cells, or in the human genome. For example, a section may comprise up to 50, up to 100, up to 150 or up to 190 of the nucleotides of SEQ ID NO:1.

The control sequence that is amplified in methods of the invention may be any suitable sequence that allows quantification of the target sequence. The control nucleic acid may be any suitable nucleic acid, eg. a single or double stranded fragment or a sequence contained within a vector, for example a plasmid vector. Preferably, the control nucleic acid is chosen so that it will undergo amplification at a substantially identical rate to that of the nucleic acid in the sample which is to be analyzed. Following amplification, measurement of the amount of amplified control sequence relative to the amount of amplified target sequence from the sample allows the quantity of nucleic acid originally present in the sample to be determined.

Accordingly, it is preferred that the control sequence is of similar length and topology to the target sequence. Thus, the control sequence may be of any length. For example, lengths of up to 50, up to 100, up to 250, up to 200 or up to 300 base pairs are preferred with lengths in the region of from 100 to 250 bp being more preferred and lengths of 180 to 220 bp being particularly preferred. The most preferred control sequence, as shown in SEQ ID NO:2, has a length of 183 base pairs, as it was obtained by introducing a SmaI recognition site into the sequence of SEQ ID NO:1.

Also, it is preferred that a control sequence of the invention has a high degree of sequence homology to the target sequence. Preferably, the control sequence has at least 70%, at least 80%, at least 90%, at least 95% or at least 99% homology with the target sequence.

Further, it is preferred that a control sequence of the invention has a similar topology to the target sequence. Thus, linear control sequences are preferred.

The difference between the target and control sequences may be in the nature of one or more nucleic acid deletions, substitutions or insertions, or may arise from any other type of nucleic acid rearrangement or sequence alteration.

In a preferred embodiment of the invention, the control nucleic acid differs from the target nucleic acid by the presence of at least one predetermined restriction enzyme recognition sequence (restriction site). Such a restriction site can be generated, for example, using a copy of the original target sequence which is altered by site-directed mutagenesis or by using oligonucleotide primers complementary to the target sequence at all residues except those which need changing to construct the desired restriction site. Such primers may have any appropriate sequence and the primer pair represented by SEQ ID NO:7 and SEQ ID NO:8 are examples of suitable sequences. These primers can be used to introduce a SmaI site into the sequence of SEQ ID NO:1, and other primers could be used to introduce other restriction sites. Following PCR amplification of the target and control sequences, the reaction mixture (or a portion thereof) is brought into contact with a restriction enzyme capable of cutting the predetermined restriction site or sites. In this way, the uncut amplified target sequence can be resolved, eg. by electrophoresis, from the two or more fragments of the cut amplified control sequence; ultimately allowing quantification of the target sequence.

It is preferred that the predetermined restriction site in the control nucleic acid is a restriction site that is unique to the control sequence, i.e. only two fragments of DNA will be produced upon digestion of the control fragment. Desirably, the predetermined restriction site is centrally located in order that the two fragments produced by digestion are of the same or of a similar size, eg. within 15, preferably 5, nucleotides in length of each other. This will mean that the two fragments produced will appear as a single band on a gel following electrophoresis. Quantitative analysis of the band will provide a determination of the total amount of amplified control DNA.

Other configurations of restriction sites are also possible. For example, the control nucleic acid may contain, for example, 2, 3, 4 or more restriction sites, one or more of which can be cut following PCR. Such multiple restriction sites may be recognition sites for the same enzyme or for two or more different enzymes. They may be located in a manner such that digestion with the appropriate enzymes produces fragments or a substantially similar size or of different sizes. Such configurations could be used to provide an internal control for the efficiency of the restriction digest or to provide fragments of convenient size for resolution. For example, a restriction site unique to the selected region of the target nucleic acid which, when cut, will divide the selected region into two unequal fragments could be eliminated from part of the control sequence region and the same restriction site introduced at a central location in the said control sequence. Following PCR and digestion with an enzyme capable of cutting this centrally located site in the control region followed by resolution by electrophoresis, three different size fragments will be seen. The amount of DNA in all three fragments may be measured and the amount of target DNA quantified. If for any reason the restriction digest is incomplete, a further amplified fragment will be seen. However, this will not affect the quantification of target nucleic acid, which can be determined simply by the ratio of digested fragments.

A further method of controlling the digest is to add to the sample, prior to digesting, a further DNA fragment containing a restriction site for the restriction enzyme which is to be used for digesting of the target DNA which is of a size such that it will not, either as a complete fragment or following digestion, be superimposed over digested or undigested control or target nucleic acid in the resolution step of the method of the invention. This can be used to monitor the efficiency of the digest. The ratio of undigested to digested further DNA can be used to correct for any incomplete restriction digests.

Although the embodiment of the invention discussed above envisages that the control region will be altered to introduce a predetermined restriction site, the invention also includes altering the control DNA to eliminate a restriction site, should a convenient restriction site occur in the target nucleic acid. Where a suitable restriction site occurs in the natural target nucleic acid, primers substantially equidistant from this site can be selected in order that the predetermined restriction site is centrally located in the selected region.

In control sequences of the invention, any type of restriction site may be exploited in the manner outlined above. In one preferred control sequence, as shown in SEQ ID NO:2, a SmaI site has been introduced. The primer portions of these nucleic acids are capable of hybridizing to sections of both the target and control sequences, owing to the high sequence homology between the target and control sequences. In principle, such hybridization may occur with any section of the target sequence as long as the primer portion is capable of hybridizing to both the target and control sequences and initiating amplification of them. Preferably, the section over which hybridization occurs comprises at least 10, more preferably at least 15 to 20, for example 16, 17, 18 or 19; at least 30; or at least 50 to 100 nucleotides. More preferably, the primer portions of the nucleic acids of the invention comprise from 10 to 15 nucleotides. The sections of the target sequence with which hybridization occurs may be located in any part of the target sequence; i.e. they may be within the sequence or at one end of it.

Optionally, the nucleic acids of the invention may also comprise a further portion, especially if the section to which the primer portion hybridizes is at the 5' end of the target sequence. The optional further portion may therefore comprise nucleotides that extend beyond the end of the target or control sequence. The length of the further portion may be up to 25, for example, up to 20, up to 18, up to 10 or up to 5 nucleotides. The sequence of the further portion may be of any nature. For example, it may be native HHV-7 nucleic acid sequence or a sequence with substantial sequence homology thereto. Alternatively, the sequence of the further portion may be an unrelated (non-HHV-7) sequence. For example, the further portion may be an amplifier strand as discussed in EP-A-0-317,077. This will allow detection of HHV-7 DNA by addition of a multimer probe comprising a first nucleic acid sequence complementary to the amplifier strand and two or more (eg. 4, 5, 6 or 7) sequences complementary to a separate labelled nucleic acid probe.

It is preferred that the primer portions will be perfectly complementary to the section of the target sequence to which they hybridise, in the sense that every nucleotide will base pair with the one with which it pairs most stably (A with T or U; C with G). However, small deviations from this rule may be allowed, so long as they do not prevent the primer from hybridising with the target and control sequences and initiating amplification. Thus, the primer portion may be, for example, up to 70%, up to 80%, up to 90%, up to 95% or up to 99% complementary to the relevant section of the target or control sequence.

Preferred primers capable of hybridising to both the target (SEQ ID NO:1) and control sequences (e.g. SEQ ID NO:2) of the invention are the primers of SEQ ID NO:3, SEQ ID NO:4, SEQ ID NO:5 and SEQ ID NO:6.

Preferably, the primers of the invention will be in isolated form, for example in aqueous solution. Thus, in samples of the primers, at least 90% at least 95% or at least 99% of the nucleic acid in the sample will typically be a single nucleic acid of the invention, or a pair of primers capable of amplifying of the target and control sequences in a PCR.

In a preferred embodiment of the invention, pairs of nucleic acids as described above are employed. Any two nucleic acids of the invention may form such a pair as long as the primer portion of one of them is capable of hybridizing to the target nucleic acid of SEQ ID NO:1 and the primer portion of the other is capable of hybridizing to the complementary strand to the target sequence, and as long as the two nucleic acids in combination are capable of initiating amplification of the target and control sequences or sections thereof. Thus, in preferred primer pairs of the invention, the two primer portions hybridize with the target nucleic acid and its complementary strand towards the 5' end of each strand. Accordingly, it is preferred that the nucleic acid molecules hybridize at a location that is from 0 to 50 nucleotides 3' to the 5' end of the sequence of SEQ ID NO:1 of the complementary strand thereto. For example, it is preferred that the 5' end of each primer portion hybridizes at a location that is from 0 to 10, from 10 to 20, from 20 to 30, from 30 to 40 or from 40 to 50 nucleotides 3' to the 5' end of the sequence of SEQ ID NO:1 or of the complementary strand thereto.

One preferred primer pair of the invention is provided by the combination of the nucleic acid molecules of SEQ ID NO:3 and SEQ ID. NO:4. Another preferred pair is represented by SEQ ID NO:5 and SEQ ID NO:6.

The invention further provides methods for detecting and quantifying the occurrence of HHV-7 in samples. Typically, these samples will comprise human tissue, cells or bodily fluids or extracts derived from such tissues, cells or fluids. Thus, for example, methods of the invention may be used to detect and/or quantitate the number of viral genomes present in a sample, quantitative methods being preferred.

Thus, methods of the invention can detect and or quantify HHV-7 under a variety of circumstances. For example, it is desirable to detect and/or quantify HHV-7 in samples taken from patients who may be infected with HHV-7. Also, methods of the invention can be used to evaluate the effectiveness of antiviral drugs. In this case, cell cultures comprising HHV-7 can be assayed using methods of the invention, the resulting information being used to determine what concentration of antiviral agent to use.

Methods according to the invention rely on amplifying target and control nucleic acids as described above by any suitable method, PCR being a preferred method. In such methods, one or more primers as described above are used to initiate amplification. Typically, primers are employed in pairs for the amplification of double stranded nucleic acid with one primer binding to a site towards the 5' end of each strand.

In general, primers, preferably primer pairs as described above, are added to the sample, as well as the control sequence. As the target and control sequences have high sequence homology, and are preferably identical at the sites to which the primers bind, one pair of the primers hybridises to both target and control sequences. Thus, PCR leads to amplification of both sequences.

For the analysis and quantification of the target nucleic acid sequence or section thereof, the predetermined amount of control sequence added may be any suitable amount, preferably an amount within a factor of $10^3$-fold of the amount of target nucleic acid suspected to be contained within the sample. In a typical reaction it is likely that between 5 and $10^5$ molecules of control sequence, eg. about 1000, will be used, although those of skill in the art will appreciate that this may vary, depending, for example, on the concentration of nucleic acid in the sample being analyzed. In order to achieve a more accurate result, a series of reactions each using a different amount of control sequence may be performed and the results compared.

Amplification, preferably by means of PCR, is then carried out. Where PCR is employed, any number of amplification cycles that amplifies the target sequence to a sufficient degree may be used, for example up to 20, up to 40 or up to 80 cycles, with from 30 to 50 cycles being preferred and 35 to 45 cycles being particularly preferred in the first round of PCR. Similarly, any suitable conditions may be used, particularly as regards types and concentrations of reagents used in the PCR reactions and temperatures in the denaturation, annealing and extension stages of the PCR reaction.

In a particularly preferred embodiment of the invention, a nested PCR reaction is used to amplify the target and control sequences. In nested PCR, two or more pairs of primers are employed sequentially to amplify progressively shorter sections of the target and control sequences. Thus, in a two-stage nested PCR, two pairs of primers are used. The first pair hybridises to the target or control nucleic acid towards the respective 5' ends of each strand. Amplification results in a nucleic acid product that is equivalent the section of the target or control sequence between the 5' ends of the two primers. A further pair of primers is then employed. These bind to the amplified product at sites that are 3' to the first primer binding sites and are thus within the first pair of primer binding sites. Thus, the nucleic acid molecules of the primer pair used in each successive amplification routine are capable of hybridizing to the target sequence of SEQ ID NO:1 in such a position that the 5' ends of the primer regions are located at least one nucleotide 3' to the site at which the 5' end of the corresponding primer of the previous pair hybridized. Preferably, the 5' end of each successive corresponding primer should hybridize to the target sequence at least 5, at least 10, at least 20 or at least 30 nucleotides 3' to the site at which the 5' end of the previous corresponding primer hybridized.

A second or subsequent amplification stage results in a shorter nucleic acid section than was obtained in the first amplification. The products of the second stage are then detected and quantified.

Nested PCR has the advantage that a greater total number of cycles of amplification can be performed without significant amplification of background contaminants (which are amplified to a small extent in many PCR reactions owing to non-specific binding of primers to sequences other than the one of interest).

This background amplification places a practical limit on the number of amplification cycles that can be achieved with any single primer pair. Nested PCR enables this limit to be overcome and lower levels of target sequence to be detected. This is particularly beneficial in clinical applications where HHV-7 may be present at very low levels in human tissues or bodily fluids. As an example of primers suitable for nested PCR according to the invention, primers HHV7-1 (SEQ ID NO:3) and HHV7-2 (SEQ ID NO:4) are suitable as the first (outer) pair of primers as they hybridise to sites close to the 5' ends of the two strands of the target sequence (SEQ ID NO:1). Primers HHV7-3 (SEQ ID NO:5) and HHV7-4 (SEQ ID NO:6) are suitable as the second (inner) pair of primers as they hybridise to sites further from the 5' ends of the two strands of the target sequence and more towards the centre of the target sequence. Second round amplification with these primers may occur for 5 to 40 cycles, with from 5 to 25 cycles being preferred and 12–20 cycles being particularly preferred.

Analysis of the products of the amplification reaction is then carried out. Quantitative analyses are preferred, though detection of the target nucleic acid sequence without quantification is also within the scope of the invention. Detection can, for example, be achieved using a single primer sequence of the invention as a probe. A single primer sequence will not act to amplify the target sequence but will, if it is sufficiently complementary, hybridise specifically to it. This specificity can be exploited, by any means known in the art (such as those of Sambrook et al; 1989, Molecular Cloning: A Laboratory Manual), to detect the presence of the target nucleic acid. For example, the probe may carry a label (e.g. a radioactive or fluorescent label) which can be detected by a suitable method.

Detection and quantification of the amplified target and control nucleic acids may be performed by any suitable means known in the art. However, certain methods of detection and quantification are preferred. In particular, methods relying on the presence of a unique restriction site in either the target or control sequence are preferred, as described above. In such methods, one sequence, typically the control sequence, includes one or more restriction sites that are absent from the other sequence. Following amplification, one or more of these distinctive restriction sites is cleaved with the appropriate restriction enzyme. The cleavage products are then identified and quantified, thus allowing quantification of the target sequence. Alternatively, the presence of the altered base can be detected by a point mutation assay (Kaye et al (1992) J. Virol. Methods) to yield the distribution of bases at the specific position represented by target or control sequence amplicons.

Preferably, the PCR amplified target and control nucleic acids or fragments thereof, such as cleaved fragments of the control nucleic acid) are resolved by electrophoresis through other methods, eg. other types of size-fractionation may be used if appropriate.

Following resolution of the target and control nucleic acids, the relative amounts of these nucleic acids may be measured by any means known in the art. Preferably, the amplified nucleic acids will contain a radioactive label or fluorescent label which can be measured by, for example, autoradiography followed by scanning densitometry or laser detection of the amplified products. The radio label may be present in the primers, or incorporated in the nucleotides used in nucleic acid synthesis during amplification reaction.

Alternatively, the amplified target and control nucleic acids can be resolved by use of oligonucleotide probes which are specific for one or the other, but not both, amplified products. As the control nucleic acid typically differs slightly from the target sequence, it is possible to synthesise probes that are specific for the amplified control nucleic acid but do not, under conditions of high stringency, hybridise to the target nucleic acid. A second probe specific for the target sequence could be used to quantify that sequence. Alternatively, a first probe specific for the target or control nucleic acid could be used to determine the quantity of one or other of these products and then a second probe specific to both products used on the same sample to ensure the total amount of nucleic acid produced. The difference between the measurement with the first probe and measurement with the probe common to both products will provide an indication of the amount of whichever of the selected and control products was not measured in the first measurement. In a further embodiment, where the difference between the control and target nucleic acids is small, a single oligonucleotide probe encompassing the region of difference and 100% homologous to a section of one or other of the two sequences could be used. At low stringency, the probe will hybridise to both the control and selected regions although at high stringency it will only hybridise to a region of 100% homology.

When amplification by PCR is used, the control and target nucleic acids will be substantially homologous. For example this may mean that besides the differences mentioned above which allow resolution of the amplified selected and control nucleic acids, there will be no other differences between the sequences. This will help to ensure equal efficiency of the reaction on both control and target sequences. However, minor alterations to the sequences may be possible without detriment to the present invention.

The nucleic acids which may be analyzed include DNA and RNA, with DNA being preferred. When RNA is being amplified by PCR, an initial reaction using a first primer and reverse transcriptase is required. The efficiency of reverse transcription can vary very significantly depending upon reaction conditions. Therefore, when the target nucleic acid is RNA, it is preferred that the control nucleic acid be RNA. Such control RNA can be generated using a control DNA sequence cloned into an RNA transcription vector which generates an RNA species using a suitable RNA polymerase in conjunction with a suitable promoter, eg a T3 or T7 promoter. The control RNA generated can be quantified using standard spectrophotometric assays. The advantage of such a system is that the efficiency of both the reverse transcription and PCR steps are controlled for.

The invention further provides isolated nucleic acid sequences related to the target and control sequences. The target and control sequences themselves are given in SEQ ID NO:1 and SEQ ID NO:2 . The section of SEQ ID NO:1 amplified by the primers of SEQ ID NO:3 and SEQ ID NO:4 is given in SEQ ID NO:9, and the 143 bp section of SEQ ID NO:1 amplified by primers of SEQ ID NO:5 and SEQ ID NO:6 is given in SEQ ID NO:10. The most preferred control sequence of the invention is given in SEQ ID NO:2. The section of SEQ ID NO:2 amplified by the primers of SEQ ID NO:5 and SEQ ID NO:6 is given in SEQ ID NO:11.

The invention also provides kits for quantification of HHV-7 in samples as described above. These kits comprise reagents suitable for performing methods as described above, and therefore for effecting detection, and preferably quantification, of HHV-7 in samples. A kit suitable for quantifying HHV-7 in a sample will. comprise a control nucleic acid, for example the control nucleic acid of SEQ ID NO:2, as described above; and one or more pairs of primers as described above that are suitable for amplifying both the target and control nucleic acid sequences, or sections thereof. Preferred kits according to the invention comprise a control nucleic acid having a restriction site not present in the target nucleic acid, as described above; for example the control nucleic acid of SEQ. ID. NO:2, which contains a SmaI site.

Preferred kits of the invention may also comprise one or more preferred primer pairs such as the primer pair represented by SEQ ID NO:3 and SEQ ID NO:4 and/or the primer pair represented by SEQ ID NO:5 and SEQ ID NO:6. Particularly preferred kits of the invention will be suitable for performing nested PCR methods employing two or more pairs of primers. Thus, for example, a preferred kit according to the invention may comprise the primer pair represented by SEQ ID NO:3 and SEQ ID NO:4together with the primer pair represented by SEQ ID NO:5 and SEQ ID NO:6. Typically, these will be provided in separate containers as they will be used in separate stages of a method according to the invention.

Kits according to the invention may also comprise any other suitable reagents, for example a restriction enzyme, such as SmaI, suitable for cleaving a control sequence comprising a restriction site not found in the target nucleic acid.

Nucleic acids of the invention are preferably DNA although other nucleic acids such as RNA may be used.

The 193 base pair fragment of the invention encodes a polypeptide homologous with the KA3L gene of HHV-6. By extension, it is therefore the positional homologue of the Herpes Simplex Virus ICP27 gene. HSV ICP27 has been shown to be an important gene in the regulation of mRNA transcripts and it is therefore a potential antiviral target, since HSV ICP27 deletion mutants do not propagate in cell culture.

Therefore, the 193 bp sequence, and the sequences of the invention that are related to it, may be useful in interrupting viral transcription. Accordingly, nucleic acid fragments having the sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11, and the complementary strands thereof, may form the basis of antiviral agents.

In particular, they may be used to prepare "antisense" DNA constructs which, when transcribed as mRNA, hybridise to the "sense" mRNA transcribed from the corresponding native viral gene, typically a HHV-7 gene, thus forming a duplex that cannot be translated into a protein and is degraded by the host cell. Thus, the expression of the native viral protein is reduced, regulation of mRNA transcripts is disrupted, and viral replication in the host cell is impaired.

For in vivo activity, antisense oligonucleotides will require modifications in the molecule's backbone and possibly additions at either the 5' or 3', or both, ends of the molecule. This is to (1) achieve resistance to degradation by DNAases, (2) enhance the potency of the molecule and (3) to enhance uptake of the oligonucleotide by cells. This is an area of intense research and development. Currently the technology exists to produce sufficient quantities of modified oligonucleotides for therapeutic use (see for example Biotechnology, November 1993, page 1225). A number of different types of modification to oligonucleotides are known in the art. These include methylphosphonate and phosphorothioate backbones (where the phospate groups in the nucleic acid backbone are replaced by methylene or sulphur) and addition of acridine or polylysine chains at the 3' and/or 5' end of the molecule. For the purpose of the present invention, it is to be understood that all or part of the oligonucleotides described herein may be modified by any method available in the art in order to enhance their in vivo activity or lifespan.

Further, it will be clear to those of skill in the art that specific oligonucleotides described herein are represented in standard notation, ie., by the letters A, C, G or T (or U) to indicate the base of the nucleotide, written in the 5' to 3' direction. Unless specified to the contrary, these sequences may be modified as described above.

The nucleic acid fragments (SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11, of the invention may be used as the basis for antiviral agents against any virus that has a suitable sequence in its genome, preferably a human herpesvirus, more preferably HHV-7.

The invention therefore provides: nucleic acid fragments of the invention for use in methods of treatment of the human or animal body by therapy, particularly with a view to treating, or preventing or ameliorating pathologies caused by viruses, especially human herpesviruses, such as HHV-7; use of nucleic acid fragments of the invention in the manufacture of medicaments for the treatment, prevention or amelioration of such viral pathologies; methods of treating, preventing or ameliorating these viral diseases by administering nucleic acid sequences of the invention alone or in combination with a pharmaceutically acceptable carrier, diluent or excipient to human or animals in need thereof; and pharmaceutical compositions comprising nucleic acid sequences of the invention and a pharmaceutically acceptable carrier, diluent or excipient.

The following examples illustrate the invention.

EXAMPLES

Example 1

Construction of Viral DNA Library

Viral DNA was extracted from infected cells by the method of Mukai et al (1994) J. Med. Virol. 42, 224–227). Virus-infected cells were lysed and total nucleic acid digested with RNase a and DNase 1. Trichlorotrifluoroethane was added and mixed vigorously, after which the precipitate was pelleted by centrifugation at 400 g for 5 min. Supernatant containing viral capsids was layered onto a discontinuous 5%/40% glycerol gradient and centrifuged at 100,000 g for 90 minutes. The pellet was digested for 3 hours at 65° C. using proteinase K in a 10 mM Tris.HCl, lmM EDTA, 0.1% SDS buffer; yielding viral DNA which was purified by standard phenol:chloroform extraction and ethanol precipitation (Sambrook et al (1989) Molecular Cloning; a laboratory manual (2nd Ed): Cold Spring Harbour Laboratory Press, New York). Three microgrammes of viral DNA was digested with 20 units HindIII at 37° C. for 18 hours in a volume of 50 µl Ligation of fragments in pUC18 was achieved using a commercially-available kit (Ready-To-go, Pharmacia, England) according to the manufacturer's protocol. Competent bacterial host E. coli was transformed by standard protocols (Sambrook et al), and quantities of cloned HHV-7 DNA were used for sequence determination. Sequencing was performed by the dideoxy method of Sanger using M13 universal primers in standardized protocols (Sambrook et al. Comparison of sequences with those of other herpesviruses was carried out using the Genetics Computer Group software examination of GEN-BANK gene databases.

Example 2

(i) PCR Primers and Reaction Conditions

A suitable clone, 193 bp in length and named 1D3 (SEQ ID NO:1) was selected and primer sequences delineating 183 bp (outer primers: SEQ ID NO:3 and SEQ ID NO:4) and 143 bp (inner primers: SEQ ID NO:5 and SEQ ID NO:6) of this sequence were synthesized (R&D Systems, Abingdon, England). PCR buffer composition was 16 mM $(NM_4)_2SO_4$, 67mM Tris-HCl (pH 8.8 at 250° C., 0.010% Tween-20 (Bioline Ltd, London/England); 2 mM $MgSO_4$; 100 ng each primer; 200 µM dATP, dCTP, dGTP, dTTP; and 1 unit Taq polymerase ("BioTaq", Bioline, London, England). Total reaction volume was 50 µl with 90 µl mineral oil overlay. Two rounds of PCR were performed, the first using the outer primers and the second using the inner primers. Thermal cycling conditions were the same for both rounds of PCR: 1 cycle at 95° C. for 6 min; 39 cycles at 94° C., 50° C., 72° C. for 30 seconds each followed by 72° C. for 10 minutes.

(ii) Construction of Control Sequence

Mutational primers HHV7-MUT5 (SEQ ID NO:7) and HHV7-MUTS (SEQ ID NO: 8) were designed spanning a suitable internal area (SEQ ID NO:2) of, but not entirely complementary to, the 1D3 sequence. Separate PCR reactions, employing respective outer primers and inner mutational primers (for example HHV7–1 and HHV7-MUT6) were optimized and used to generate amplimers with overlapping sequences of the original 1D3 clone but with a SmaI site introduced FIG. 1, A). The two reaction products were mixed in equimolar proportions (FIG. 1, B), denatured at 95° C. for 10 minutes and allowed to reanneal at room temperature for 30 minutes FIG. 1, C). Klenow fragment of DNA polymerase was used to synthesize the complementary strand from the overlap in the presence of 200 µM dNTPs and enzyme buffer in a total volume of 100 µl (FIG. 1, D). After separation of the complete double-stranded product from excess primers, enzyme and dNTPs by using a commercially-available column (Qiaquick, Qiagen, England), the construct was further amplified by using the two complementary outer primers FIG. 1, E). After similar purification the construct was ligated into the pUC18 plasmid vector (Ready-to-go, Pharmacia, England) followed by transformation of competent E. coli by standard protocols (Sambrook et a. Characterisation of suitable clones consisted of size analysis of excised fragments, linearization of plasmid by Sma1 digestion, and sequencing of the inserts by the dideoxy method of Sanger (Sambrook et al.

(iii) Qualitative PCR on Saliva Samples
(see Table 1)

Figure 1A:
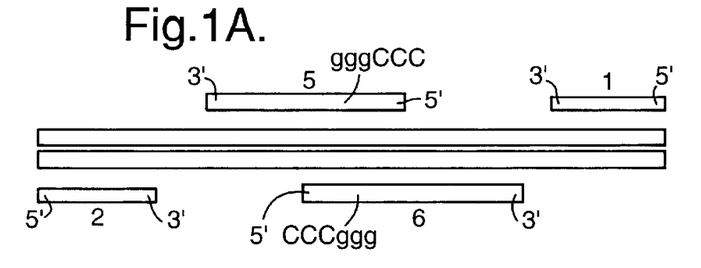
FIGS. 1A–1E. Construction of the 183bp control sequence of SEQ ID NO:2.
Figure 1B:
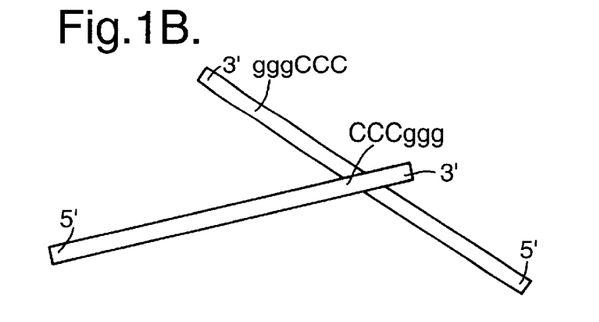
Figure 1C:
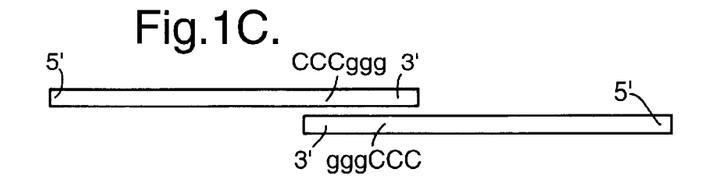
Figure 1D:
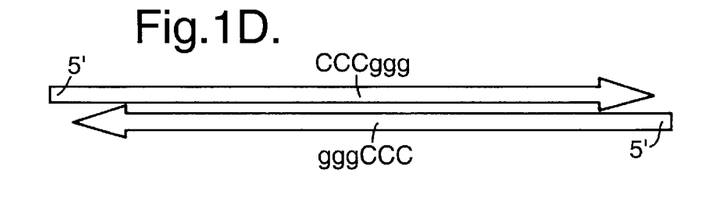
Figure 1E:
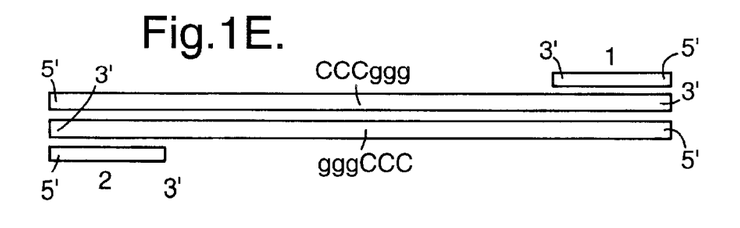
Figure 2:
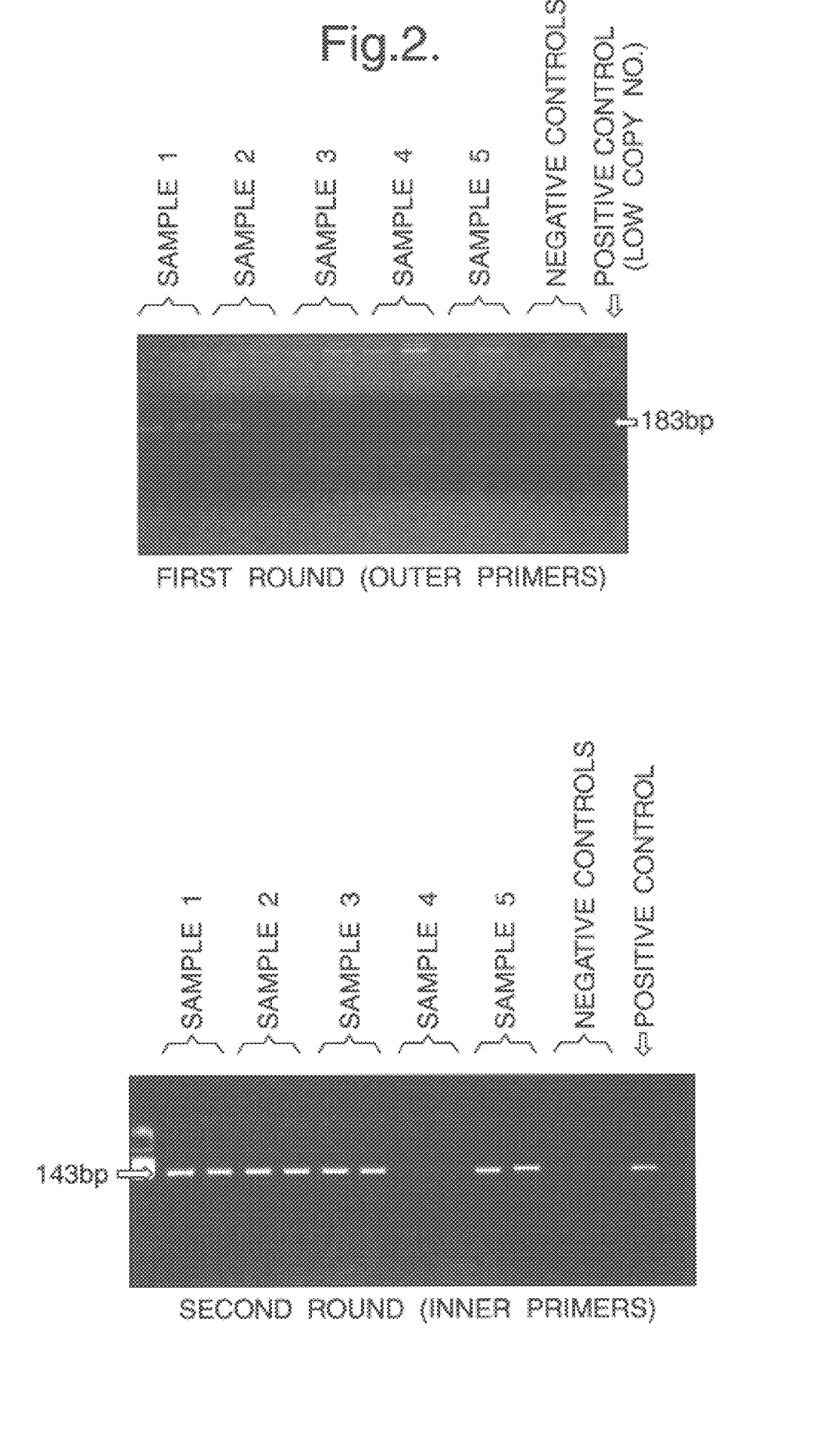
FIG. 2. Results of qualitative PCR on saliva samples, using the inner and outer primers of the invention.

PCR was performed, using the conditions described in (i) above, on saliva samples from 5 patients. The results are shown in FIG. 2. Following one round of amplification with the outer primers of SEQ ID NO:3 and SEQ ID NO:4, a band was identified on an agarose gel. This corresponded in size to the 183 bp fragment expected to result from the amplification.

Following a second round of amplification with the inner primers of SEQ ID NO:5 and SEQ ID NO:6, a band corresponding in size to the expected 143 bp fragment was strongly visualized on an agarose gel in all but one of the samples. This shows that the primers and methods of the invention readily detect HHV-7 DNA in practice.

All patients except the PCR negative individual were positive for HHV-7 antibodies using an immunofluorescence assay based on patient sera reactivity against HHV-7 injected SupTl cells. Primers were used at standard protocol amounts (100 ng) and 30 µl of whole saliva was used in a 50 µl total PCR mixture.

TABLE 1

DETECTION OF HHV-6 AND HHV-7 IN SALIVA FROM HEALTHY
VOLUNTEERS: COMPARISON WITH ANTIBODY STATUS

| Volunteer No. | HHV-6 SALIVA PCR | HHV-6 SERO-STATUS | HHV-7 SALIVA PCR | HHV-7 SERO-STATUS |
|---|---|---|---|---|
| 1 | + | + | + | + |
| 2 | + | + | − | − |
| 3 | + | + | + | + |
| 4 | + | + | + | + |
| 5 | + | + | + | + |
| 6 | − | − | + | + |
| 7 | + | + | + | + |
| 8 | + | + | + | + |
| 9 | + | + | + | + |
| 10 | + | + | + | + |
| 11 | + | + | + | + |
| 12 | + | + | + | + |
| 13 | + | + | + | + |
| 14 | + | + | + | + |
| 15 | + | + | + | + |
| 16 | + | + | + | + |

Thirty microliters saliva tested by nested PCR for HHV-6 for HHV-6 and HHV-7. Sera screened at a dilution of 1:10 by indirect immunoflurescence assays.

Example 3

Standard curve and reproducibility of the quantitative assay.

Figure 3:
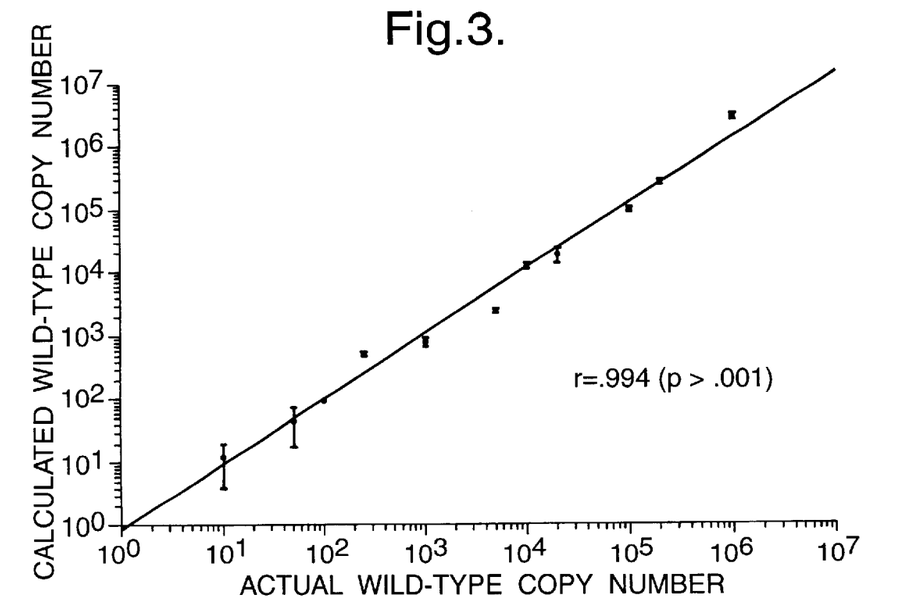
FIG. 3. Demonstration that the assay of the invention gives accurate data on samples with known genomic equivalents.

The ability of the HHV-7 quantitative assay to give accurate data on samples with known genomic equivalents is illustrated in FIG. 3. In this experiment, known copy numbers of plasmid containing the wild-type target ranging from 10 to 1,000,000 copies were co-amplified with copy numbers of control sequence in the appropriate range (10-fold more or less than the target sequence). The calculated wild-type copy number was then plotted against the actual input copy number, with each data point representing a mean of three experiments. Linear regression analysis showed that the calculated and actual copy numbers were highly correlated (R=0.994; p<0.001).

Example 4

Cross-sectional and Longitudinal Analysis of HHV-7 Viral Burden in Blood

Figure 4:
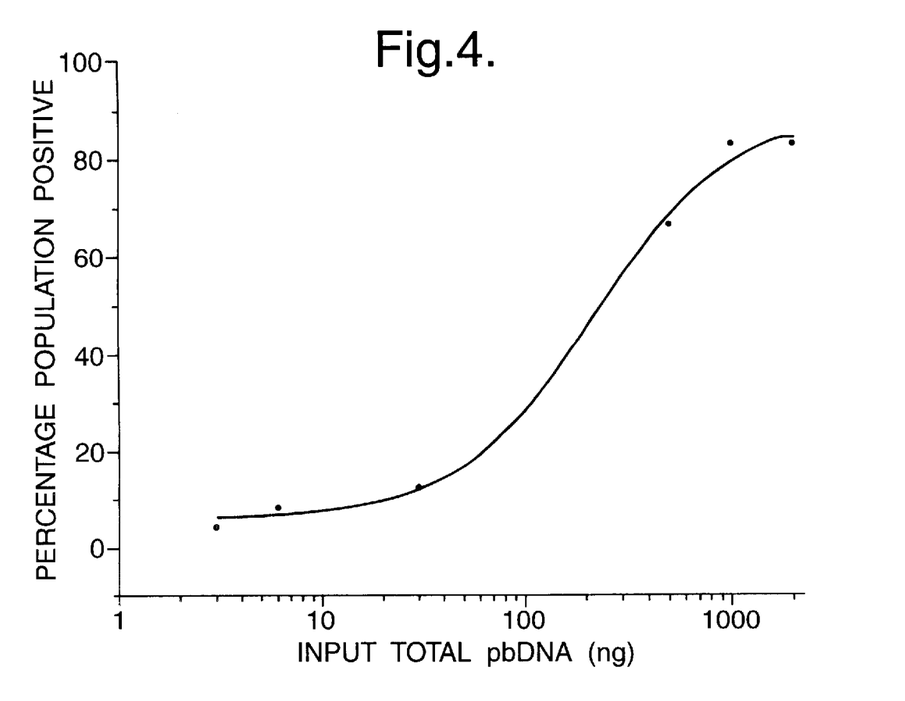
FIG. 4. Prevalence of HHV-7 DNA in blood samples from HHV-7 seropositive individuals varies according to the quantity of input DNA used for analysis.

The prevalence of HHV-7 DNA in blood samples from HHV-7 seropositive individuals varies according to the quantity of input DNA used for analysis. Therefore, at inputs of 10 to 15 ng PBMC DNA the prevalence of HHV-7 DNA is between 10% and 12% of the seropositive population, whereas when 1 $\mu$g of input DNA is used, 90% of seropositive individuals were found to contain HHV-7 DNA in their blood. These data are summarised in FIG. 4. Using the PCR conditions inherent within this patent application, these results have implications for the detection of HHV-7 DNA in normal and in immunocompromised hosts to detect levels of viral DNA commensurate with reactivation/reinfection, rather than detection of latent viral DNA.

Figure 5:
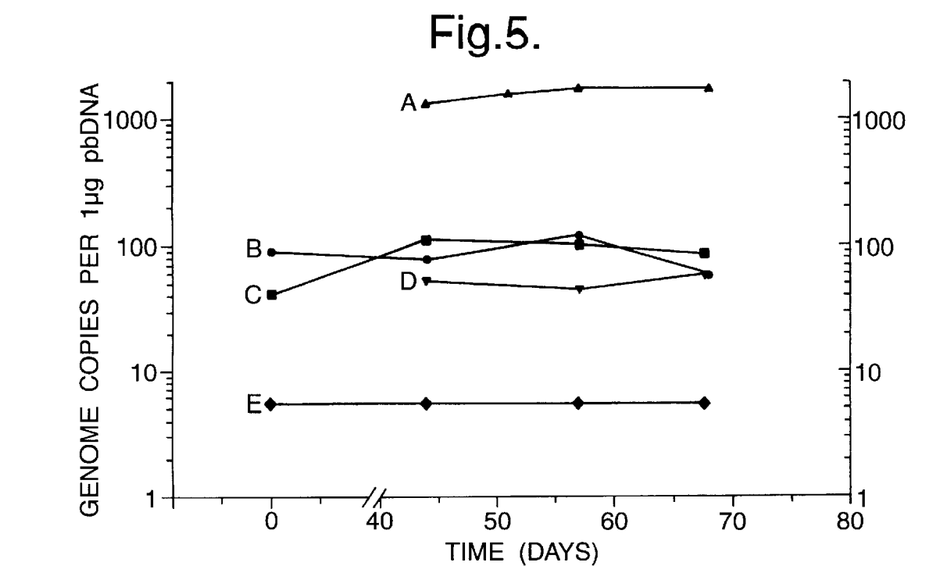
FIGS. 5 & 6. Longitudinal analysis of HHV-7 viral load in saliva and peripheral blood of healthy volunteers shows that the amount of virus remains relatively constant over time.
Figure 6:
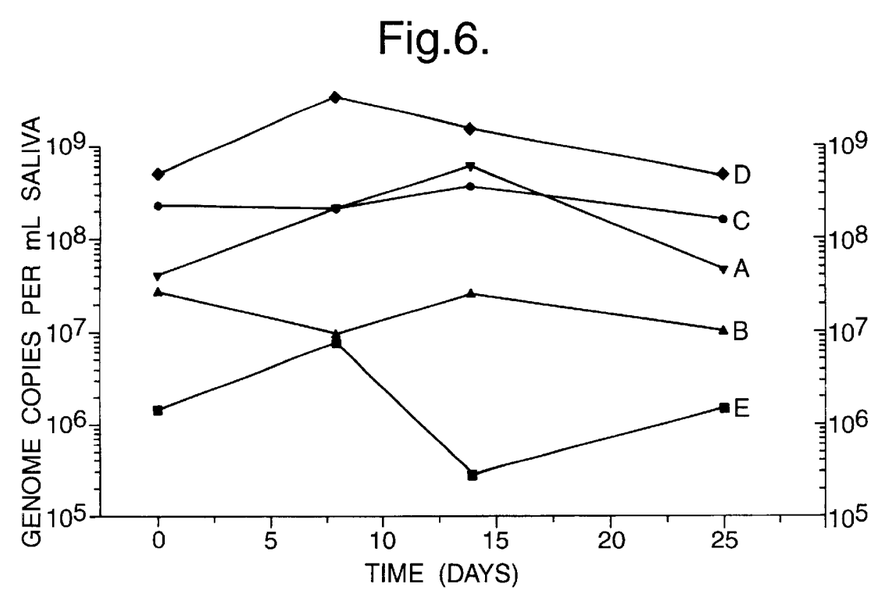

Longitudinal analysis of HHV-7 viral load in the saliva and peripheral blood of healthy volunteers showed that the amount of virus remains relatively constant over time (see FIGS. 5 and 6).

Example 5

Detection of HHV-7 DNA in the Blood of Immunocompromised Patients

Figure 7:
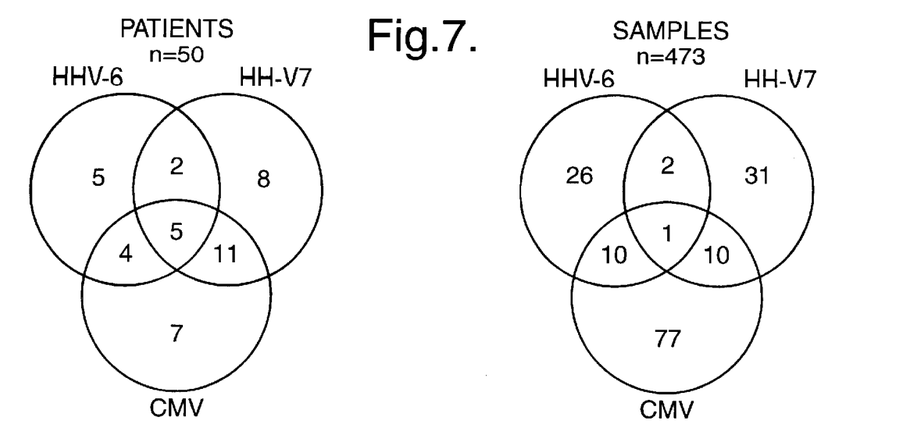
FIGS. 7, 8 & 9. Qualitative detection of HHV-7 in live, renal and bone marrow transplant recipients.
Figure 8:
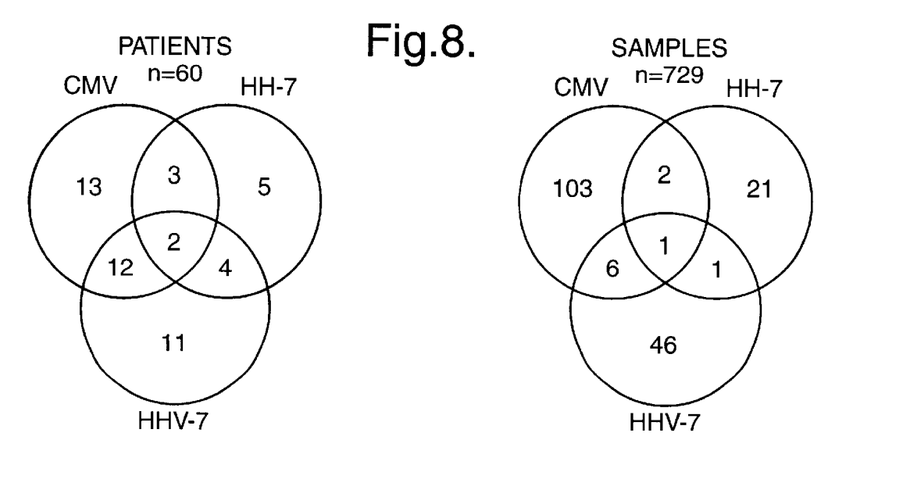
Figure 9:
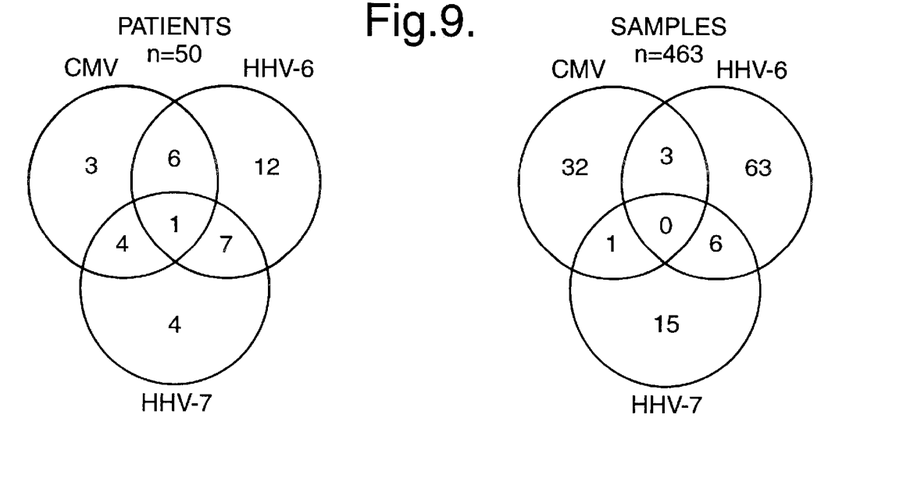

The qualitative and quantitative PCR methods described in this patent have been used to detect and measure HHV-7 in liver, bone marrow and renal transplant recipients, and HIV-infected patients.

a) Qualitative presence of HHV-7 DNA in 40 ng of peripheral blood surveillance samples from immunocompromised patients.
   i) HHV-7 in transplant recipients
      The results of the qualitative detection of HHV-7 in liver, renal and bone marrow transplant recipients on a sample and patient basis are shown in FIGS. 7, 8 & 9, respectively. For comparative purposes, the detection rates for HHV-5 (cytomegalovirus) and HHV-6 are also shown in these Venn diagranms. HHV-7 was detected in 26/50 (52%) liver patients, 29/60 (48%) renal patients and 16/50 (34%) of the bone marrow transplant recipients. On a sample basis, 44/473 (9.3%) of samples from the liver patients, 53/729 (7.4%) of samples from the renal transplant patients, and 22/651 (3.4%) of samples from bone marrow transplant recipients were positive for HHV-7.
   ii) HHv-7 in HIV-infected individuals.
      The prevalence of HHV-7 in patients with HIV infections stratified according to CD4 cell numbers is shown in Table 2. A reduction in the overall prevalence of HHV-7 DNA in the peripheral blood was observed on progressing from a CD4 strata of >700 $\mu$L to <200 $\mu$L.

TABLE 2

DETECTION OF HHV-6 OR HHV-7 IN 473 SAMPLES COLLECTED
FROM 160 HIV-POSITIVE PATIENTS

| Number (%) samples PCR-positive for: | CD4 cells per cubic milimeter | | | | |
| --- | --- | --- | --- | --- | --- |
|  | <200 | 200–400 | 400–700 | >700 | TOTALS |
| HHV-6 | 8*/136 (5.9%) | 3/164 (1.8%) | 9/129 (6.9%) | 2/44 (4.5%) | 22/473 (4.6%) |
| HHV-7 | 3*/136 (2.2%) | 1/164 (0.61%) | 4/129 (3.1%) | 3/44 (6.8%) | 11/473 (2.3%) |

*One sample PCR-positive for both HHV-6 and HHV-7 b) HHV-7 load in liver transplant recipients
   The maximum virus load detected during surveillance of liver transplant recipients is shown in FIG. 9. Maximum viral loads for HHV-7 were similar to those for HHV-6, both of which were substantially lower than for CMV.

c) Clinicopathological Correlations of HHV-7 infection in liver transplant recipients
   In contrast to other betaherpesviruses, our investigations have shown very few pathological consequences of HHV-7 infection in the liver transplant recipients to date.

Example 6

Detection and Quantification of HHV-7 DNA in Children with Febrile Illness

Figure 10:
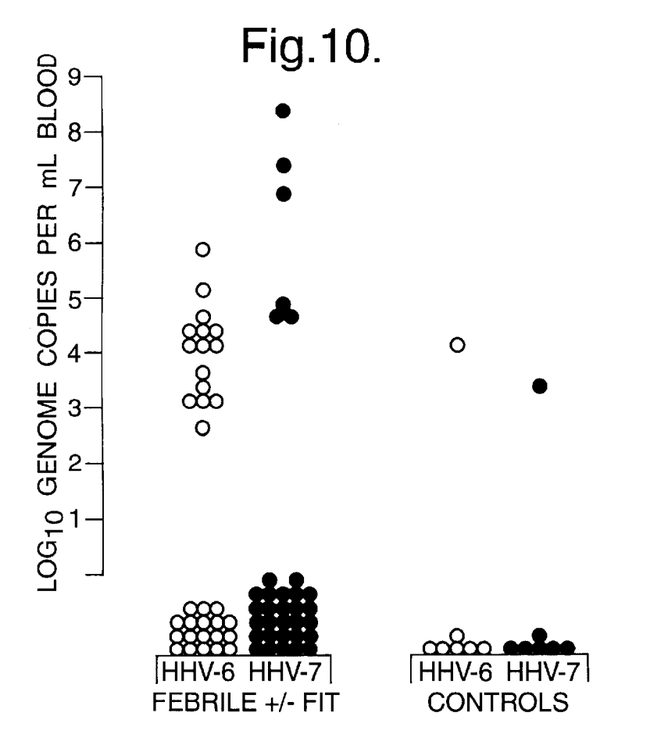
FIG. 10. HHV-6 and HHV-7 blood viral load versus clinical syndrome.

Forty children aged between 6 months - 24 months with febrile illness have been investigated for the presence of HHV-7 DNA as a marker of primary infection relating to the clinical appearance of exanthem subitum-like disease. Six of these children had HHV-7 DNA in their blood, with a median viral load of 4,300,000 genomes/ml (range 57,000–290,000,000; FIG. 10). Careful inspection of the results of PCR on saliva from these individuals revealed that 3 were highly likely to be experiencing primary infection with HHV-7. These 3 children possessed the highest viral load of the group (median 32,000,000 genomes/ml), which was approximately 100-fold higher than the median viral load for HHV-6 in children undergoing primary HHV-6 infection (138,000 genomes/ml of blood).

Example 7

Figure 11:
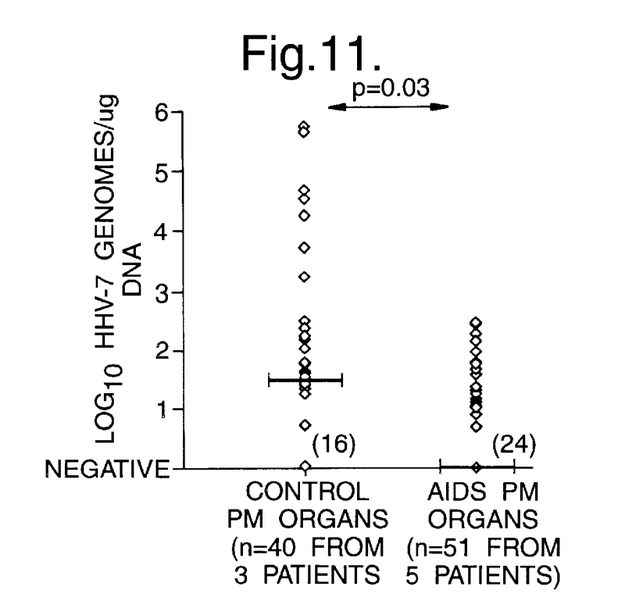
FIG. 11. HHV-7 load in organs at death.

Prevalence and Quantity of HHV-7 in Necropsy Tissue from AIDS Patients and Control Subjects DNA extracts (10 μg) from organs obtained at necropsy were used as a substrate for HHV-7 DNA analysis by the qualitative and quantitative PCR methods described in this patent. Although HHV-7 DNA was detected in 59/125 (47%) of tissues from AIDS patients, it was at a significantly lower viral load than that presenting in control subjects (median HHV-7 load in controls 24 genomes/μg DNA; range 0 to 550,000), whereas in AIDS patients (median =0 genomes/μg DNA; range 0 to 295; Mann-Whitney test: p<0.001). These data are shown in FIG. 11.

Sequence Information
Target and Control Sequences
SEQ ID NO:1. 193 bp Target Sequence
AAGCTTTTTA CATTTGGCTT GCTTTTTGGT TTG-TAAATTC AATTGGACGG TTTGCTTAGA TTGCTGT-GAA GCAAAGCTGC AAGACGGAGT TGTAGAACAT GCAACATTAA AGCTGTTGTA CTCTTCAGGC ATGT-TAGGAT GCAGACCAAA CTCCATAAAT TCTTTGG-GAA GATAGGTACA GAAATATAAG CTT
SEQ ID NO:2. 183 bp Control Sequence
TTTTTACATT TGGCTTGCTT TTTGGTTTGT AAAT-TCAATT GGACGGTTTG CTTAGATTGC TGTGAAG-CAA AGCTGCAACC CGGGGTTGTA GAACATGCAA CATTAAAGCT GTTGTACTCT TCAGGCATGT TAG-GATGCAG ACCAAACTCC ATAAATTCTT TGGGAA-GATA GGTACAGAAA TAT
Outer (first round) Primers
HHV7-1 5' TTT TTA CAT TTG GCT TGC TTT TTG 3' (SEQ ID NO:3)
HHV7-2 5' ATA TTT CTG TAC CTA TCT TCC CAA 3' (SEQ ID NO:4).
Inner (second round) Primers
HHV7-3 5' TGC TTT TTG GTT TGT AAA TTC 3' (SEQ ID NO:5)
HHV7-4 5' GAA TTT ATG GAG TTT GGT CTG 3' (SEQ ID NO:6)
Mutational Primers
HHV7-MUT5 5' CAA AGC TGC AAC CCG GGG TTG TAG AAC A 3' (SEQ ID NO:7)
HHV7-MUT6 5' TGT TCT ACA ACC CCG GGT TGC AGC TTT G 3' (SEQ ID NO:8)
Amplified Sequences
SEQ ID NO:9. The section of SEQ ID NO:1 amplified by primers of SEQ ID NO:3 and SEQ ID NO:4
TTTTTA CATTTGGCTT GCTTTTTGGT TTGTAAATTC AATTGGACGG TTTGCTTAGA TTGCTGTGAA GCAAAGCTGC AAGACGGAGT TGTAGAACAT GCAACATTAA AGCTGTTGTA CTCTTCAGGC ATGT-TAGGAT GCAGACCAAA CTCCATAAAT TCTTTGG-GAA GATAGGTACA GAAATAT
SEQ ID NO:10. The section of SEQ ID NO:1 amplified by primers of SEQ ID NO:5 and SEQ ID NO:6
T GCTTTTTGGT TTGTAAATTC AATTGGACGG TTTGCTTAGA TTGCTGTGAA GCAAAGCTGC AAGACGGAGT TGTAGAACAT GCAACATTAA AGCT-GTTGTA CTCTTCAGGC ATGTTAGGAT GCAGAC-CAAA CTCCATAAAT TC
SEQ ID NO:11. The section of SEQ ID NO:2 amplified by primers of SEQ ID NO:5 and SEQ ID NO:6
CAA AGCTGCAACC CGGGGTTGTA GAACA

---

What is claimed is:

1. A method of determining the amount of a target nucleic acid having the sequence shown in SEQ ID NO:1 in a sample which method comprises:
   (i) mixing the sample with a predetermined amount of control nucleic acid;
   (ii) bringing the mixture formed in (i) into contact with a pair of nucleic acid molecules each comprising:
      a primer portion consisting of a contiguous sequence of from 10 to 50 nucleotides that hybridizes to (a) the target nucleic acid molecule represented by SEQ ID NO:1, or (b) to the complement of the molecule of SEQ ID NO:1 in a polymerase chain reaction (PCR) buffer comprising 16 mM $(NH_4)_2SO_4$, 67 mM Tris-HCl (pH 8.8 at 25° C.), 0.01% Tween-20, 2 mM $MgSO_4$ at 50° C.; and optionally a further portion comprising from 1 to 25 nucleotides joined to and immediately 5' to the 5' end of the primer portion
      wherein one nucleic acid molecule has a primer portion of type (a) and the other nucleic acid molecule has a primer portion of type (b); and wherein the two primers in combination amplify the target nucleic acid molecule represented by SEQ ID NO:1, or a section thereof, in a polymerase chain reaction;
   (iii) performing a nucleic acid amplification reaction, said reaction requiring the presence of the primer portions defined in (ii) to amplify the target nucleic acid sequence or a section thereof and the control nucleic acid or a section thereof;
   (iv) determining the relative quantities of the amplified control and target nucleic acids; and
   (v) calculating from the determination of (iv) the amount of target nucleic acid in the sample.

2. A method according to claim 1 wherein amplification is performed by means of a polymerase chain reaction (PCR).

3. A method according to claim 2 wherein the control nucleic acid comprises at least one restriction site not present in the target sequence and wherein the determination performed in step (iv) comprises the step of cleaving one or more such restriction sites.

4. A method according to claim 3 wherein the restriction site is a SmaI site.

5. A method according to claim 4 wherein the control nucleic acid comprises the sequence shown in SEQ ID NO:2 or any section thereof containing a restriction site not present in the sequence of SEQ ID NO:1.

6. The method according to claim 1 wherein, in step (i), the nucleic acid molecule of type (a) is the nucleic acid molecule of SEQ ID NO:3 and the nucleic acid molecule of type (b) is the nucleic acid molecule of SEQ ID NO:4; or the nucleic acid molecule of type (a) is the nucleic acid molecule of SEQ ID NO:5 and the nucleic acid molecule of type (b) is the nucleic acid molecule of SEQ ID NO:6.

7. The method according to claim 1 wherein the pair of nucleic acid molecules of step (ii) respectively hybridize to the target nucleic acid sequence of SEQ ID NO:1 and its complementary strand in such positions that the 5' end of each primer portion hybridizes at a location that is from 0 to 50 nucleotides 3' to the 5' end of the sequence of SEQ ID NO:1 or the 5' end of the complement of the nucleic acid molecule of SEQ ID NO:1.

8. A method according to claim 1 wherein contacting step (ii) and amplification step (iii) are performed at least one further time, each time using a further different pair of nucleic acid molecules; the nucleic acid molecules of the pair used in each successive contacting and amplification routine hybridizing to the target sequence of SEQ ID NO:1 in such a position that the 5' ends of the primer regions are located at least one nucleotide 3' to the site at which the 5' end of the previous pair hybridizes; such that the PCR performed is a nested PCR.

9. A method according to claim 8 wherein contacting step (ii) and amplification step (iii) are performed twice such that there is a first round of contacting (ii) and amplification (iii) and a second round, with the nucleic acid pair of claim 5 being employed in the first round and the nucleic acid pair of claim 6 being employed in the second round.

10. The method according to claim 8 wherein the first nucleic acid molecule of type (a) is the nucleic acid molecule of SEQ ID NO:3 and the first nucleic acid molecule of type (b) is the nucleic acid molecule of SEQ ID NO:4.

11. The method according to claim 8 wherein the second nucleic acid molecule of type (a) is the nucleic acid molecule of SEQ ID NO:5 and the second nucleic acid molecule of type (b) is the nucleic acid molecule of SEQ ID NO:6.

12. The method according to claim 8 wherein the different pair of molecules hybridizes to the target nucleic acid sequence of SEQ ID NO:1 and its complementary strand in such positions that the 5' end of each primer portion hybrizes at a location that is from 0 to 50 nucleotides 3' to the 5' end of the sequence of SEQ ID NO:1 or the 5' end of the complement of the nucleic acid molecule of SEQ ID NO:1.

13. A kit for quantification of human herpesvirus 7 (HHV-7) in a sample, which kit comprises:
   (i) a pair of nucleic acid molecules according to claim 6 that amplifies both the target sequence and a control nucleic acid sequence, or sections thereof; and
   (ii) the control nucleic acid sequence.

14. A kit according to claim 13 which further comprises (iii) a further pair of nucleic acid molecules according to claim 2 that hybridize to the target sequence of SEQ ID NO:1 in such a position that the 5' ends of the primer portions of said further pair of nucleic acid molecules are located at least one nucleotide 3' to the site at which the 5' end of said pair of primers according to claim 13 hybridizes.

15. A kit according to claim 14 comprising: (i) a control sequence of SEQ ID NO:2, (ii) a pair of nucleic acids of SEQ ID NO:3 and SEQ ID NO:4, and (iii) a pair of nucleic acids of SEQ ID NO:5 and SEQ ID NO:6.

16. The kit according to claim 13 wherein the control nucleic acid comprises at least one restriction site not present in the target sequence.

17. The kit according to claim 16 wherein the restriction site is a SmaI site.

18. The kit according to claim 17 wherein the control sequence comprises the sequence shown in SEQ ID NO:2 or any section thereof containing a restriction site not present in the sequence of SEQ ID NO:1.

19. The kit according to claim 13 wherein the pair of nucleic acid molecules hybridizes to the target nucleic acid sequence of SEQ ID NO:1 and its complementary strand in such positions that the 5' end of the each primer portion hybridizes at a location that is from 0 to 50 nucleotides 3' to the 5' end of the sequence of SEQ ID NO:1 or the 5' end of the complementary strand thereto.

20. The kit according to claim 13 wherein the nucleic acid molecule of type (a) is the nucleic acid molecule of SEQ ID NO:3 and the nucleic acid molecule of type (b) is the nucleic acid molecule of SEQ ID NO:4.

21. The kit according to claim 13 wherein the nucleic acid molecule of type (a) is the nucleic acid molecule of SEQ ID NO:5 and the nucleic acid molecule of type (b) is the nucleic acid molecule of SEQ ID NO:6.

22. A pair of nucleic acid molecules each comprising:

(i) a primer portion consisting of a contiguous sequence of 10 to 50 nucleotides which hybridizes to (a) a target nucleic acid molecule represented by SEQ ID NO:1, or (b) the complement of the nucleic acid molecule of SEQ ID NO:1 in a polymerase chain reaction (PCR) buffer comprising 16 mM $(NH_4)_2SO_4$, 67 mM Tris-HCl (pH 8.8 at 25° C.), 0.01% Tween-20, 2 mM $MgSO_4$ at 50° C.; and optionally (ii) a further portion comprising from 1 to 25 nucleotides joined to and immediately 5 ' to the 5' end of the primer portion;

wherein one nucleic acid molecule comprises a primer portion of type (a) and the other nucleic acid molecule comprises a primer portion of type (b); and wherein the two primers in combination amplify the target nucleic acid molecule represented by SEQ ID NO:1, or a portion thereof, in a polymerase chain reaction.

23. A pair of nucleic acid molecules according to claim 22 wherein the nucleic acid molecule of type (a) is the nucleic acid molecule of SEQ ID NO:3 and the nucleic acid molecule of type (b) is the nucleic acid molecule of SEQ. ID NO:4.

24. A pair of nucleic acid molecules according to claim 22 wherein the nucleic acid molecule of type (a) is the nucleic acid molecule of SEQ ID NO:5 and the nucleic acid molecule of type (b) is the nucleic acid molecule of SEQ. ID NO:6.

25. A pair of nucleic acid molecules according to claim 2 that, respectively, hybridize to the target nucleic acid sequence of SEQ ID NO:1 and its complementary strand in such positions that the 5' end of the each primer portion hybridizes at a location that is from 0 to 50 nucleotides 3' to the 5' end of the sequence of SEQ ID NO:1 or the 5' end of the complement of the nucleic acid molecule of SEQ ID NO:1.

26. A nucleic acid molecule selected from the group consisting of

5' TTT TTA CAT TTG GCT TGC TTT TTG 3' (SEQ ID NO:3);

5' ATA TTT CTG TAC CTA TCT TCC CAA 3' (SEQ ID NO:4);

5' TGC TTT TTG GTT TGT AAA TTC 3' (SEQ ID NO:5); and

5' GAA TTT ATG GAG TTT GGT CTG 3' (SEQ ID NO:6).

27. An isolated nucleic acid molecule selected from the group consisting of the sequences shown in SEQ ID NO:1, SEQ ID NO:2, SEQ ID NO:9, SEQ ID NO:10 and SEQ ID NO:11 (CAAAGCTGCAACCCGGGGTTGTAGAACA); and the complementary strands thereof.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 193 base pairs
      (B) TYPE: nucleic acid
      (C) STRANDEDNESS: double
      (D) TOPOLOGY: linear    (ii) MOLECULE TYPE: DNA (genomic)

(xi) SEQUENCE DESCRIPTION: SEQ ID NO:1:

```
AAGCTTTTTA CATTTGGCTT GCTTTTTGGT TTGTAAATTC AATTGGACGG TTTGCTTAGA      60

TTGCTGTGAA GCAAAGCTGC AAGACGGAGT TGTAGAACAT GCAACATTAA AGCTGTTGTA     120

CTCTTCAGGC ATGTTAGGAT GCAGACCAAA CTCCATAAAT TCTTTGGGAA GATAGGTACA     180

GAAATATAAG CTT                                                        193
```

(2) INFORMATION FOR SEQ ID NO:2:

(i) SEQUENCE CHARACTERISTICS:
      (A) LENGTH: 183 base pairs (B) TYPE: nucleic acid
            (C) STRANDEDNESS: double
            (D) TOPOLOGY: linear (ii) MOLECULE TYPE: other nucleic acid
            (A) DESCRIPTION: /desc = "amplified control sequence"

(xi) SEQUENCE DESCRIPTION: SEQ ID NO:2:

TTTTTACATT TGGCTTGCTT TTTGGTTTGT AAATTCAATT GGACGGTTTG CTTAGATTGC      60

TGTGAAGCAA AGCTGCAACC CGGGGTTGTA GAACATGCAA CATTAAAGCT GTTGTACTCT     120

TCAGGCATGT TAGGATGCAG ACCAAACTCC ATAAATTCTT TGGGAAGATA GGTACAGAAA     180

TAT                                                                  183

(2) INFORMATION FOR SEQ ID NO:3:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(xi) SEQUENCE DESCRIPTION: SEQ ID NO:3:

TTTTTACATT TGGCTTGCTT TTTG                                            24

(2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(xi) SEQUENCE DESCRIPTION: SEQ ID NO:4:

ATATTTCTGT ACCTATCTTC CCAA                                            24

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(xi) SEQUENCE DESCRIPTION: SEQ ID NO:5:

TGCTTTTTGG TTTGTAAATT C                                               21

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(xi) SEQUENCE DESCRIPTION: SEQ ID NO:6:

```
GAATTTATGG AGTTTGGTCT G                                                    21

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:7:

CAAAGCTGCA ACCCGGGGTT GTAGAACA                                             28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:8:

TGTTCTACAA CCCCGGGTTG CAGCTTTG                                             28

(2) INFORMATION FOR SEQ ID NO:9:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "amplified target sequence"

(xi) SEQUENCE DESCRIPTION: SEQ ID NO:9:

TTTTTACATT TGGCTTGCTT TTTGGTTTGT AAATTCAATT GGACGGTTTG CTTAGATTGC          60

TGTGAAGCAA AGCTGCAAGA CGGAGTTGTA GAACATGCAA CATTAAAGCT GTTGTACTCT         120

TCAGGCATGT TAGGATGCAG ACCAAACTCC ATAAATTCTT TGGGAAGATA GGTACAGAAA         180

TAT                                                                      183

(2) INFORMATION FOR SEQ ID NO:10:

(i) SEQUENCE CHARACTERISTICS:
        (A) LENGTH: 143 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "amplified target sequence"

(xi) SEQUENCE DESCRIPTION: SEQ ID NO:10:

TGCTTTTTGG TTTGTAAATT CAATTGGACG GTTTGCTTAG ATTGCTGTGA AGCAAAGCTG          60

CAAGACGGAG TTGTAGAACA TGCAACATTA AAGCTGTTGT ACTCTTCAGG CATGTTAGGA         120

TGCAGACCAA ACTCCATAAA TTC                                                143

(2) INFORMATION FOR SEQ ID NO:11:
```

-continued

```
    (i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "amplified target sequence"

(xi) SEQUENCE DESCRIPTION: SEQ ID NO:11:

CAAAGCTGCA ACCCGGGGTT GTAGAACA                                              28
```